(12) United States Patent
Tozaka

(10) Patent No.: US 6,391,347 B1
(45) Date of Patent: May 21, 2002

(54) METHOD OF MANUFACTURING AN AROMATIC ANTI-BACTERIAL AGENT CONTAINING HINOKITIOL

(75) Inventor: Eisaku Tozaka, Kyoto (JP)

(73) Assignee: Topics Co., Ltd., Kyoto (JP)

( * ) Notice: Subject to any disclaimer, the term of this patent is extended or adjusted under 35 U.S.C. 154(b) by 62 days.

(21) Appl. No.: 09/686,075

(22) Filed: Oct. 12, 2000

Related U.S. Application Data

(62) Division of application No. 09/487,991, filed on Jan. 20, 2000.

(30) Foreign Application Priority Data

Feb. 3, 1999 (JP) .............................................. 11-026138

(51) Int. Cl.⁷ ................................................ A01N 65/00
(52) U.S. Cl. ...................................... 424/770; 424/725
(58) Field of Search .................................. 424/770, 725

(56) References Cited

U.S. PATENT DOCUMENTS

| 5,419,896 A | 5/1995 | Bunczij et al. |
|---|---|---|
| 5,811,114 A | 9/1998 | Knight et al. |
| 6,183,748 B1 * | 2/2001 | Tozaka ........................ 424/770 |

FOREIGN PATENT DOCUMENTS

| JP | 59-085279 | 5/1984 |
|---|---|---|
| JP | 7-89819 | 4/1995 |
| JP | 8-66172 | 3/1996 |
| JP | 9-136992 | 5/1997 |
| JP | 9-143045 | 6/1997 |

OTHER PUBLICATIONS

Computer Cropu Abstract JP2001059097 "Production of Aomori hiba cypress material as building material for preventing termintes and in agricultural fields, comprising removing cypress tree bark and ry distilling to obtaining hinokitol or hiba cypress oil".*

* cited by examiner

*Primary Examiner*—Herbert J. Lilling
(74) *Attorney, Agent, or Firm*—Banner & Witcoff, Ltd.

(57) ABSTRACT

The present invention provides a method of manufacturing an aromatic anti-bacterial agent containing hinokitiol, comprising the steps of extracting an aqueous solution containing at least hinokitiol from wood chips and reducing the aqueous solution extracted to produce the aromatic anti-bacterial agent.

2 Claims, No Drawings

METHOD OF MANUFACTURING AN AROMATIC ANTI-BACTERIAL AGENT CONTAINING HINOKITIOL

This application is a divisional of Ser. No. Divisional of 09/487,991, filed Herewith (Jan. 20, 2000).

FIELD OF THE INVENTION

This invention relates to a method of manufacturing an aromatic anti-bacterial agent with anti-bacterial and bactericidal effects, for instance, containing hinokitiol as its principal ingredient.

BACKGROUND OF THE INVENTION

A variety of pathogenic and other bacteria may be found in our surroundings, i.e., in our everyday living spaces, and it is known that these bacteria may be killed or their growth may be prevented by the spraying or application of hinokitiol extracted from the linoki (Japanese cypress), the thuja or the like.

Hinokitiol is a substance produced via extraction from hinoki and can be used at no risk to humans or animals. It has been proven to have anti-bacterial and bactericidal properties and is also effective against ticks and mildew. Clinically, hinokitiol has been shown to be effective for patients with atopic dermatitis; it also functions against dermatophytosis, actinomycosis and the bacteria that cause athlete's foot, and further guards against and eliminates unpleasant odors.

There has been growing use of the properties of hinokitiol in recent years. One typical application is aromatic anti-bacterial agents intended for interior use; hinokitiol is a principal ingredient in such agents.

However, if an aqueous solution containing hinokitiol, as extracted from hinoki, is employed without any processing or dilution, the scent of the hinokitiol can be overpowering to some. In other words, when the extracted aqueous solution is used in undiluted form, the hinokitiol has a powerful fragrance; if the solution adheres to the room's walls, furniture, etc., the fragrance can remain at undiminished strength for some time. If this fragrance is too strong, it cancels out other fragrances in the room (e.g., from flowers), resulting in an unattractive overall smell. Processing methods to reduce the strength of the fragrance are available; however, they have the undesirable effect of weakening the properties of the hinokitiol, and in particular, its usefulness as an anti-bacterial and bactericidal product.

SUMMARY OF THE INVENTION

The object of this invention is to eliminate disadvantages mentioned above.

In order to achieve this object, a method of manufacturing an aromatic anti-bacterial agent containing hinokitiol is used, in which an aqueous solution containing at least hinokitiol is extracted from wood chips, then reduced to produce an aromatic anti-bacterial agent.

If the above process is followed, the extracted aqueous solution containing hinokitiol presents alkalinity when reduced, thus weakening the scent of the hinokitiol and enhancing the solution's bactericidal and anti-bacterial properties.

The aromatic anti-bacterial agent obtained has a milder fragrance, even when applied to the skin, and does not give off a scent incompatible with its surroundings. Furthermore, the agent's enhanced anti-bacterial properties allow it to be used effectively against various types of dermatitis, etc.

The reduction process can be carried out easily by immersing inert electrodes in the extracted aqueous solution until the oxidation-reduction potential declines to a predetermined level that is lower than at the start of immersion. Lowering the oxidation-reduction potential in this manner allows the reduction process to be controlled via the length of immersion time of the inert electrodes, thus simplifing the reduction process. The predetermined potential is a negative potential approximately 40 times or less that of the oxidation-reduction potential at the start of immersion.

DETAILED DESCRIPTION OF THE PREFERRED EMBODIMENTS

The following describes an embodiment of the invention.

An aqueous solution containing hinokitiol is extracted by separating it from a solution containing a mix of oil and aqueous solution, obtained by directing high-pressure, high-temperature flow of steam at raw material comprised of wood fragments, e.g. hinoki chips, bark, branches or leaves, to fumigate the raw material, followed by rapid cooling and liquefaction of the steam containing the hinokitiol. The raw material comprised of wood fragments of hinoki is thus reduced to approximately sawdust-sized particles, which enhances extraction efficiency as by increasing the surface area of the overall supply of the raw material, i.e., the area available for contact with the steam.

The solution extracted, i.e. the undiluted extract, contains a mixture of oil and aqueous solution containing hinokitiol. This undiluted extract is accumulated in a container used for extraction, the oil is separated, and the aqueous solution is separated from the oil and placed in a separate vessel to obtain an aqueous solution containing at least hinokitiol. This aqueous solution may of course also contain other beneficial extracts apart from hinokitiol.

Next, the aqueous solution obtained is reduced. Specifically, inert electrodes made from a material such as platinum are first immersed in the solution. The inert electrodes may be of a type in general use in the field of the art and consist for example of thin metal plates square in shape, of platinum/magnesium alloy, zinc alloy and copper alloy. The inert electrodes are positioned at a suitable distance from each other in parallel on the same axis. Immersing the inert electrodes in the aqueous solution causes oxidation-reduction potential to be generated on the inert electrodes. This oxidation-reduction potential decreases as the aqueous solution is reduced. Generally, if the inert electrodes are left in the aqueous solution over a 24-hour period, the oxidation-reduction potential falls to a predetermined level which is a negative potential forty times or less the negative oxidation-reduction potential at the start of immersion. When the inert electrodes have been left in the aqueous solution for some 24 hours, they are removed from the aqueous solution. This completes the reduction process used to obtain an aromatic anti-bacterial agent containing hinokitiol.

By reducing in this way an aqueous solution which is an aqueous part of the aromatic anti-bacterial agent from raw materials and which contains at least hinokitiol the distinctive fragrance of hinokitiol can be lessened. Such the aromatic anti-bacterial agent also possesses enhanced anti-bacterial properties compared to solutions that have not been subject to reduction.

Tables 1 and 2 show the results of trials conducted to evaluate the bactericidal ability of the aromatic anti-bacterial agent containing hinokitiol obtained by this method. The evaluation was conducted as follows: using the Phenol Coefficient Method, 5 ml of aromatic anti-bacterial agent containing hinokitiol was inoculated with 0.1 ml of $10^6$ bacteria solution and the bacteria population measured over time at 20° C. In this evaluation experiment, the number of live bacteria was measured every one hour after commencing experiment. The initial number of bacteria was measured by inoculating 5 ml of a phosphoric acid buffer solution (1/15 M pH 7.2) with 0.1 ml of bacteria solution.

The bacteria stock used were *Escherichia coli*; bacteria stock number IFO-3972, *Pseudomonas aeruginosa*; IFO-12689, MRSA (Methicillin resistant *Staphylococcus aureus*; KB-1005 (MRSA)), and *Enterococcus faecalis*; IFO-12580. Media used were Mueller Hinton II and a sheep's blood agar culture (BBL).

Table 1 shows the results of these evaluation trials of bactericidal ability, and Table 2 the results of a control experiment conducted for the purposes of comparison.

TABLE 1

(Results of trial)

Change in bacteria numbers over time

| Bacterium | Start | 1 hr-1 | 1 hr-2 | 1 hr-3 | Average |
| --- | --- | --- | --- | --- | --- |
| E-coli | $5.1 \times 10^5$ | $2.7 \times 10^2$ | $3.3 \times 10^2$ | $3.6 \times 10^2$ | $3.2 \times 10^2$ |
| Ps. aeruginosa | $4.7 \times 10^5$ | $4.3 \times 10^2$ | $3.9 \times 10^2$ | $3.9 \times 10^2$ | $4.0 \times 10^2$ |
| MRSA | $5.6 \times 10^5$ | 10 or less | 10 or less | 10 or less | 10 or less |
| En. faecalis | $5.0 \times 10^5$ | $2.6 \times 10^5$ | $3.9 \times 10^5$ | $2.3 \times 10^5$ | $2.9 \times 10^5$ |

Unit: CFU/ml

TABLE 2

(Results of control experiment)

Change in bacteria numbers over time

| Bacterium | Start | 1 hr-1 | 1 hr-2 | 1 hr-3 | Average |
| --- | --- | --- | --- | --- | --- |
| E-coli | $5.1 \times 10^5$ | $5.1 \times 10^5$ | $5.1 \times 10^5$ | $5.1 \times 10^5$ | $5.1 \times 10^5$ |
| Ps. aeruginosa | $4.7 \times 10^5$ | $4.7 \times 10^5$ | $4.7 \times 10^5$ | $4.7 \times 10^5$ | $4.7 \times 10^5$ |
| MRSA | $5.6 \times 10^5$ | $5.5 \times 10^5$ | $5.6 \times 10^5$ | $5.6 \times 10^5$ | $5.6 \times 10^5$ |
| En. faecalis | $5.0 \times 10^5$ | $5.0 \times 10^5$ | $5.0 \times 10^5$ | $5.0 \times 10^5$ | $5.0 \times 10^5$ |

Unit: CFU/ml

As is apparent from Table 1, bacteria populations of all types decreased over time. This decrease was particularly marked in the case of MRSA, with no bacteria growth observed after one hour. Furthermore, as the results of the control experiment in Table 2 indicate, no change was observed in the numbers of any of the bacteria types after one hour. These results therefore clearly demonstrate that the bacteria were killed by the aromatic anti-bacterial agent containing hinokitiol.

The aromatic anti-bacterial agent containing hinokitiol was therefore observed to possess excellent bactericidal and anti-bacterial capabilities. In addition, the distinctive fragrance of hinokitiol was milder than that given off by a raw, unprocessed version of the substance. This aromatic anti-bacterial agent containing hinokitiol can therefore be used in rooms on a regular basis without a hinokitiol fragrance permeating the room to an overpowering degree, and is also effective in protecting rooms against bacteria, and in removing bacteria. The agent is particularly effective against MRSA, killing off bacteria so efficiently that no growth is detected an hour after application, making it ideal for use in hospitals to effectively prevent MRSA infection. Furthermore, because the fragrance of the aromatic anti-bacterial agent containing hinokitiol is not overpowering when used indoors, it can be inhaled without creating any sense of excessive concentration, providing the same calming effect in the home or in hospitals as breathing in forest air.

The invention is not restricted to the embodiment described above.

Moreover, each of the arrangements is not restricted to the embodiment, but there may be various modifications and changes without departing from the scope and spirit of the invention.

What is claimed is:

1. An aromatic anti-bacterial product containing hinokitiol, produced by a method comprising the steps of extracting an aqueous solution containing at least hinokitiol from wood chips and reducing the aqueous solution extracted to produce the aromatic anti-bacterial agent.

2. An aromatic anti-bacterial product containing hinokitiol as claimed in claim 1, wherein the reducing step is carried out by immersing inert electrodes into the aqueous solution extracted until the oxidization-reduction potential reaches a predetermined level lower than that at the start of immersion.

* * * * *